United States Patent [19]

Whitekettle et al.

[11] Patent Number: 4,995,987

[45] Date of Patent: Feb. 26, 1991

[54] ENHANCEMENT OF THE EFFICACY OF ANTIMICROBIALS BY THE ADDITION OF ANIONS CAPABLE OF INTERFERING WITH MICROBIAL ELECTROCHEMICAL REACTIONS

[75] Inventors: Wilson K. Whitekettle, Conroe, Tex.; John T. Conlan, Ventura, Calif.

[73] Assignee: Betz Laboratories, Inc., Trevose, Pa.

[21] Appl. No.: 410,765

[22] Filed: Sep. 21, 1989

[51] Int. Cl.$^5$ ............................................. C02F 1/50
[52] U.S. Cl. ................................. 210/754; 210/755; 210/760; 210/763; 210/764
[58] Field of Search .............. 210/754, 764, 765, 916, 210/755, 756, 760, 762, 763, 766

[56] References Cited

U.S. PATENT DOCUMENTS

| | | | |
|---|---|---|---|
| 3,702,298 | 11/1972 | Zsoldos, Jr. .......................... | 210/62 |
| 3,843,545 | 10/1974 | Heuston .............................. | 252/181 |
| 4,108,790 | 8/1978 | Foroulis ............................... | 210/754 X |
| 4,495,200 | 1/1985 | Lindstrom et al. ................. | 210/764 X |
| 4,561,981 | 12/1985 | Characklis ......................... | 210/764 X |
| 4,719,083 | 1/1988 | Baker et al. ........................ | 210/764 X |
| 4,802,994 | 2/1989 | Mouché et al. ................... | 210/764 X |

OTHER PUBLICATIONS

"The Mechanisms of Inhibition of Desulfovibrio and Desulfotomaculum Species by Selenate and Molybdate", Journal of Applied Bacteriology, 65, Nov. 1988, pp. 419–423, P. J. Newport, et al.

"Chemical Mitigation of Corrosion by Chlorine Dioxide in Oil Field Water Floods", Materials Performance, May 1985, pp. 45–50, W. Prues et al.

Primary Examiner—Tom Wyse
Attorney, Agent, or Firm—Alexander D. Ricci; Gregory M. Hill

[57] ABSTRACT

A method of enhancing the efficacy of anti-microbial chemical compounds in an aqueous medium comprising adding an anionic chemical species to the medium. The anion acts as a competing electron receptor of the terminal cellular reduction reaction. This results in a weakening of the microorganism leaving it more vulnerable to effective action by the anti-microbial chemical.

12 Claims, No Drawings

ENHANCEMENT OF THE EFFICACY OF ANTIMICROBIALS BY THE ADDITION OF ANIONS CAPABLE OF INTERFERING WITH MICROBIAL ELECTROCHEMICAL REACTIONS

FIELD OF THE INVENTION

The present invention relates to applications where chemical agents are utilized as antimicrobials in an aqueous medium.

BACKGROUND OF THE INVENTION

Various aqueous systems contain microorganisms which exhibit either aerobic or anaerobic metabolic activity. The presence of these microorganisms may result from natural conditions, such as would occur from the normal multiplication of microbes in aqueous environments, or from the accidental introduction of microbes, such as sulfate-reducing bacteria (SRB) found in the oil processing industry.

The unchecked proliferation of the microbial population results in numerous unacceptable conditions, such as odor problems, safety hazards (from $H_2S$ generation), the buildup of excessive deposits and the fouling of processing equipment in contact with the aqueous medium. In order to prevent these problems, antimicrobial chemical agents are utilized to control the growth of the microbes.

Aerobic and anaerobic microorganisms having a respiratory metabolism biochemically oxidize either organic or inorganic chemical compounds in order to obtain energy for growth and reproduction. These are enzymatically mediated chemical oxidations and must be coupled with chemical reductions in order for the reactions to continue. This process is actually a series of oxidation/reduction steps culminating in a terminal reduction reaction which balances the initial oxidation reaction. The terminal reduction is usually that of the reduction of $O_2$ to $H_2O$ in aerobes and may be a number of reactions in anaerobes (e.g., $SO_4^= \rightarrow H_2S$ for some sulfate reducing bacteria, such as Desulfovibrio).

Oxidizing and non-oxidizing antimicrobials affect microorganisms in many various modes of action which usually have little to do with inhibiting the terminal reduction reaction. It has been discovered, in accordance with the present invention, that the addition of compounds capable of competing with the compound normally used by a microorganism as its terminal electron acceptor slows the biochemical reduction process by virtue of this competition for the electrons generated by the substrate oxidations.

The efficiency of these compounds as a competing terminal oxidant may vary and perhaps may even be less efficient than the usual terminal oxidant. Nonetheless, regardless of the degree of efficiency of the terminal oxidant, the ability of the microorganism to generate cellular energy such as ATP, is severely affected. An antimicrobial added to the system would have greater efficacy against a weakened group of microorganisms laboring in an environment concentrated with compounds competing for the available electrons.

PRIOR ART

Various techniques are known for treating water. Exemplary is U.S. Pat. No. 3,843,545 (Heuston) which discloses a composition comprising an oxidizing agent, an acid, iodide and iodate. The sterilizing effect is derived from liberated iodine and the oxidizing agent (e.g., potassium permanganate or potassium dichromate).

A method of maintaining an oxidizing environment compatible with chlorine is disclosed in U.S. Pat. No. 3,702,298 (Zsoldos, Jr., et. al.). A peroxy type salt such as sodium peroxydisulfate is combined with a multivalent catalyst such as copper or silver. The three step mechanism involves, (1) the oxidation of the metal to its trivalent state, (2) the reduction of the metal to its divalent state and (3) re-oxidation as in step 1.

In an article entitled "The Mechanisms of Inhibition of Desulfovibus and Desulfotomaculum Species by Selenate and Molybdate", Journal of Applied Bacteriology 1988, 65, p.419–423, by P. J. Newport et. al., the results of a study on selenate and molybdate as inhibitors of the growth of Sulfate Reducing Bacteria (SRB) is disclosed. The authors conclude that these two compounds inhibit the transport of sulfate thereby making the sulfate unavailable to support the growth of this type of microorganism.

In water systems where chlorine dioxide solutions are present to control bacterial proliferation, the use of other compounds to prevent chlorine dioxide corrosion on metal surfaces is described in the publication entitled, "Chemical Mitigation of Corrosion by Chlorine Dioxide in Oilfield Waterfloods", W. Prues, et. al, Materials Performance, May 1985, pp. 45-50. These compounds include arsenate, arsenite, borate, chromate, dichromate, ferrocyanide, molybdate, permanganate, phosphate, polyphosphate, silicate, tunqstate and zinc and are utilized because of their ability to lay down a protective coating on metallic surfaces which inhibits corrosive attack by chlorine dioxide.

DETAILED DESCRIPTION OF THE INVENTION

In accordance with the invention, it has been discovered that the efficacy of antimicrobial agents in various water systems, such as cooling, steam generating, gas scrubbing, paper and pulp processing, cutting fluids and oilfield waterfloods is enhanced by the addition of selected anionic compounds. Microbial energy production is dependent on having a terminal reduction step in the organism's metabolism which is usually based on the reduction of $O_2$, sulfate or nitrate. In certain environments, such as oilfield waterfloods, sulfate reducing bacteria, as the name implies, reduce $SO_4$ to generate $H_2S$. Since $H_2S$ is corrosive to oilfield processing equipment, hazardous to health and noxious to the olfactory senses, compounds such as chlorine, usually in the form of hypochlorite and chlorine dioxide, are utilized to eliminate the microbials. This is turn eliminates the generation of $H_2S$.

There are certain conditions where an anti-microbial compound may not affect the reduction of sulfate to $H_2S$. This is due to the anti-microbial being rendered non-toxic as a result of its reaction with the $H_2S$ or other reduced compounds present in the system. It has been discovered in accordance with the present invention that the addition of oxidized anion compounds to the medium provides competing species for the electrons made available by the microorganism thereby slowing the reduction of sulfate to $H_2S$. The lack of $H_2S$ renders the environment less corrosive and provides for improved anti-microbial efficacy due to the reduction of $H_2S$/anti-microbial reactions.

Oxidized anion compounds capable of acting as terminal electron acceptor substitutes for the compounds normally utilized increase anti-microbial compound efficacy against both aerobic and anaerobic microbes, especially in systems treated with oxidizing anti-microbials such as $Cl_2$, $ClO_2$, BrCl, ozone, bromo and chloro substituted halogenated triazines and the like. Compounds acting as substitute terminal electron acceptors are chromate, dichromate, molybdate, tungstate, nitrate, nitrite, phosphate and selenate. It is well known to use these compounds for the purpose of inhibiting corrosion caused by chlorinated compositions. The method of operation in this instance involves the laying down of a passive oxide film on the metal surface thereby protecting it from corrosive attack by chlorine dioxide or related compounds. It is truly unexpected to find, as disclosed herein, that the compounds identified above may be added to oilfield water-floods to substantially augment the efficacy of anti-microbials such as chlorine dioxide and the like.

The ability of Desulfovibrio to generate ATP from the substrate oxidations is impaired by the addition of an oxidized anion as a replacement for sulfate. The electrons generated by the substrate oxidation must be consumed by an equal rate reduction of sulfate. When the oxidized anion species replaces the sulfate, the enzyme system for reducing sulfate becomes inefficient or non-functional. Once the terminal reduction reaction is impaired or ceases, the substrate oxidation step is inhibited resulting in a partial or complete shut down in the generation of ATP.

The terminal reduction step is enzyme mediated and does not occur spontaneously. If it was spontaneous, the substitution of sulfate with an oxidized anion might not adversely affect the cell. Its energy producing function would continue unimpeded. With Desulfovibrio, the addition of the oxidized anions poisons the cell's ultimate terminal reduction enzyme system thereby shutting down the cell's energy producing system. Once in this weakened state, the cell easily falls prey to the anti-microbial compounds.

A study was conducted to evaluate the comparative efficacies of the various oxidized anion compounds. Furthermore, test results were obtained which show the effect on anti-microbial function when the oxidized anion compounds are combined with known anti-microbial compounds.

The anions chosen for this study were chromate, dichromate, molybdate, tungsate, nitrate, phosphate and selenate. The antimicrobials selected were chlorine (as hypochlorite) and chlorine dioxide. Desulfovibrio was used as the test organism due to its prevalence in oilfield water systems and its role in generating corrosive $H_2S$.

The test parameters are as follows. A medium was prepared which is suitable for supporting the growth of *Desulfovibrio desulficans*, a common SRB. The ingredients are:

| | |
|---|---|
| Peptone | 5.0 g |
| Beef Extract | 3.0 g |
| Yeast Extract | 0.2 g |
| Mg $SO_4$ | 1.5 g |
| $Na_2$ $SO_4$ | 1.5 g |
| Fe($NH_4$)$_2$ ($SO_4$)$_2$ | 0.1 g |
| Glucose | 5.0 g |
| Tap Water | 1.0 g |
| pH is adjusted to 7.0 | |

The various chemicals are added to this medium, and similary may be added in full scale practice, either independently or as an anion/antimicrobial combination. Strong growth on the part of Desulfovibrio is represented by increased turbidity and blackening of the medium. This is due to the production by the microbe of FeS from Fe($NH_4$)$_2$ ($SO_4$)$_2$. Effective anion compounds prevent $S^-$ formation and the correlating production of FeS, which ultimately inhibits Desulfovibrio growth. Test sample observation was terminated after 7 days.

Table I provides data on the individual efficacies of various anionic and anti-microbial compounds at inhibiting Desulfovibrio growth. Effective concentration ranges vary between the compounds. The anions selenate and dichromate and the anti-microbial chlorine dioxide all show effective inhibition at 75 ppm.

The anti-microbial endpoints, representing total inhibition of Desulfovibrio growth, for the complete set of oxidant/anion combination are listed in Tables IIA & IIB. The synergistic effects of various anion/oxidant combinations are evident. One of these combinations is $ClO_2$ and selenate. Each compound independently was effective at inhibiting growth at a concentration of 75 ppm. However, when combined, a concentration of 25 ppm of each of the individual compounds proved to be efficacious. Clearly, as Tables IIA & IIB show, selective combinations of anions/oxidants produce synergistic anti-microbial properties.

Table III provides a summary of the test results of the individual anion and oxidant compounds and the anion/oxidant combinations.

TABLE I

| Compound | \multicolumn{18}{c}{Efficacy of Individual Compounds (Concentration - ppm)} |
|---|---|

| Compound | 25 | 30 | 35 | 40 | 50 | 75 | 100 | 150 | 200 | 250 | 300 | 350 | 400 | 500 | 1000 | 2500 | 5000 | 10000 | 20000 |
|---|---|---|---|---|---|---|---|---|---|---|---|---|---|---|---|---|---|---|---|
| Molybdate | + | + | + | + | + | + | + | + | + | − | | | | − | − | | | | |
| | + | + | + | + | + | + | + | + | + | − | | | | − | − | | | | |
| Tungstate | + | + | + | + | + | + | + | + | + | | + | + | | + | + | | | | |
| | + | + | + | + | + | + | + | + | + | | + | + | | + | + | | | | |
| Selenate | + | + | + | + | + | − | − | | | − | − | | | − | | | | | |
| | + | + | + | + | + | − | − | | | − | − | | | − | | | | | |
| Chromate | + | | | | + | + | + | − | − | − | − | | − | − | | | | | |
| | + | | | | + | + | + | − | − | − | − | | − | − | | | | | |
| Dichromate | + | | | | + | − | − | − | − | − | − | | − | − | | | | | |
| | + | | | | + | − | − | − | − | − | − | | − | − | | | | | |
| Nitrate | | | | | | | | | | | | | | + | + | + | + | − | − |
| Phosphate | | | | | | | | | | | | | | + | + | .+ | + | − | − |
| | | | | | | | | | | | | | | + | + | + | + | + | − |
| | | | | | | | | | | | | | | + | + | + | + | + | − |
| Hypochlorite | + | | | | + | | + | + | − | − | − | | | − | | | | | |
| | + | | | | + | | + | + | − | − | − | | | − | | | | | |
| Chlorine | + | | | | + | − | − | − | − | − | − | | | | | | | | |
| Dioxide | + | | | | + | − | − | − | − | − | − | | | | | | | | |
| Biological | + | | | | | | | | | | | | | | | | | | |

TABLE I-continued

| Compound | Efficacy of Individual Compounds (Concentration - ppm) | | | | | | | | | | | | | | | | | | |
|---|---|---|---|---|---|---|---|---|---|---|---|---|---|---|---|---|---|---|---|
| | 25 | 30 | 35 | 40 | 50 | 75 | 100 | 150 | 200 | 250 | 300 | 350 | 400 | 500 | 1000 | 2500 | 5000 | 10000 | 20000 |
| Control | + | | | | | | | | | | | | | | | | | | |

+ = Growth
− = No Growth

TABLE IIA

Efficacy of Anion/Hypochlorite Combinations

| | Hypochlorite | | | | | | | | | | | | | | | | |
|---|---|---|---|---|---|---|---|---|---|---|---|---|---|---|---|---|---|
| Anion | Anion | | | | | | | | | | | | | | | | |
| Concentration | 50 ppm | | | | | | 75 ppm | | | | | | | 100 ppm | | | |
| ppm | 25 | 50 | 75 | 100 | 200 | 500 | 25 | 50 | 75 | 100 | 2500 | 5000 | 10000 | 25 | 50 | 75 | 100 |
| Molybdate | | + | | + | − | | − | − | | − | | | | − | − | | − |
| | | + | | + | − | | − | − | | − | | | | − | − | | − |
| Tungstate | | + | | | + | + | | | | | | | | | + | | + |
| | | + | | | + | + | | | | | | | | | + | | + |
| Selenate | + | + | | | | | − | − | | | | | | − | − | | − |
| | + | + | | | | | − | − | | | | | | − | − | | − |
| Chromate | | + | + | − | | | − | − | − | | | | | − | − | − | |
| | | + | + | − | | | − | − | − | | | | | − | − | − | |
| Dichromate | + | + | − | | | | − | − | − | | | | | − | − | − | |
| | + | + | − | | | | − | − | − | | | | | − | − | − | |
| Nitrate | | | | | | | | | | | − | − | − | | | | |
| Phosphate | | | | | | | | | | | − | − | − | | | | |
| | | | | | | | | | | | + | + | + | | | | |
| | | | | | | | | | | | + | + | + | | | | |
| Biological | + | | | | | | | | | | | | | | | | |
| Control | + | | | | | | | | | | | | | | | | |

+ = Growth
− = No Growth

TABLE IIB

Efficacy of Anion/Chlorine Dioxide Combinations

| | Chlorine Dioxide | | | | | | | | | | | | | | | | | | | |
|---|---|---|---|---|---|---|---|---|---|---|---|---|---|---|---|---|---|---|---|---|
| Anion | Anion | | | | | | | | | | | | | | | | | | | |
| Concentration | 25 ppm | | | | 50 ppm | | | | | | | | | | 75 ppm | | | | | |
| ppm | 10 | 25 | 50 | 75 | 10 | 25 | 50 | 75 | 100 | 200 | 300 | 2500 | 5000 | 10000 | 100 | 200 | 300 | 2500 | 5000 | 10000 |
| Molybdate | + | − | − | | + | − | − | | | | | | | | | | | | | |
| | + | − | − | | + | − | − | | | | | | | | | | | | | |
| Tungstate | + | + | + | | + | + | + | | + | + | + | | | | + | + | + | | | |
| | + | + | + | | + | + | + | | + | + | + | | | | + | + | + | | | |
| Selenate | + | − | − | − | + | + | − | − | | | | | | | | | | | | |
| | + | − | − | − | + | + | − | − | | | | | | | | | | | | |
| Chromate | + | + | + | | + | − | − | | | | | | | | | | | | | |
| | + | + | + | | + | − | − | | | | | | | | | | | | | |
| Dichromate | + | + | + | | + | − | − | | | | | | | | | | | | | |
| | + | + | + | | + | − | − | | | | | | | | | | | | | |
| Nitrate | | | | | | | | | | | | − | − | − | | | | + | − | − |
| | | | | | | | | | | | | − | − | − | | | | − | − | − |
| Phosphate | | | | | | | | | | | | + | + | + | | | | + | + | + |
| | | | | | | | | | | | | + | + | + | | | | + | + | + |

TABLE III

Summary of Oxidant/Anion Efficacy

| | Individual | HOCl | | | ClO$_2$ | |
|---|---|---|---|---|---|---|
| Anion | Concentration | 50 ppm | 75 ppm | 100 ppm | 25 ppm | 50 ppm |
| Molybdate | 300 ppm | 200 ppm | 25 ppm | 25 ppm | 25 ppm | 25 ppm |
| Tungstate | 1,000 ppm | NE | NT | NT | NE | NE |
| Selenate | 75 ppm | NE | 25 ppm | 50 ppm | 25 ppm | 50 ppm |
| Chromate | 150 ppm | 100 ppm | 25 ppm | 25 ppm | NE | 25 ppm |
| Dichromate | 75 ppm | 75 ppm | 25 ppm | 25 ppm | NE | 25 ppm |
| Nitrate | 10,000 ppm | NT | 2500 ppm | NT | NT | 2500 ppm |
| Phosphate | 20,000 ppm | NT | NE | NT | NT | NE |
| Hypochlorite | 200 ppm | | | | | |
| Chlorine Dioxide | 75 ppm | | | | | |

NE: Not Efficacious
NT: Not Tested

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A method of enhancing the efficacy of an antimicrobial compound selected from the group consisting of chlorine, chlorine dioxide, bromochlorine, ozone, bromo substituted hydantoins, chloro substituted hydantoins and halogenated triazines which is added to an aqueous medium to inhibit the growth of sulfate reducing bacteria comprising adding to said aqueous medium an anion compound selected from the group consisting of molybate, tungstate, selenate, chromate, dichromate, nitrate and phosphate in combination with said antimicrobial compound.

2. A method according to claim 1 wherein said sulfate reducing bacteria is *Desulfobibrio desulfuricans*.

3. A method according to claim 1 wherein said aqueous medium is a cooling system.

4. A method according to claim 1 wherein said aqueous medium is a steam generating system.

5. A method according to claim 1 wherein said aqueous medium is a gas scrubbing system.

6. A method according to claim 1 wherein said aqueous medium is an oilfield waterflood.

7. A method according to claim 1 wherein said antimicrobial chemical compound is chlorine and said anion compound is molybdate.

8. A method according to claim 1 wherein said antimicrobial chemical compound is chlorine dioxide and said anion compound is molybdate.

9. A method according to claim 1 wherein said antimicrobial chemical compound is chlorine and said anion compound is selenate.

10. A method according to claim 1 wherein said antimicrobial chemical compound is chlorine dioxide and said anion compound is selenate.

11. A method according to claim 1 wherein said antimicrobial chemical compound is chlorine and said anion compound is chromate.

12. A method according to claim 1 wherein said antimicrobial chemical compound is chlorine dioxide and said anion compound is chromate.

* * * * *